United States Patent [19]

Fahim

[11] 4,073,289
[45] Feb. 14, 1978

[54] METHOD OF MALE CONTRACEPTION FOR DOMESTIC MAMMALS HAVING A SCROTUM

[76] Inventor: Mostafa S. Fahim, 500 Halen Drive, Columbia, Mo. 65201

[21] Appl. No.: 682,062

[22] Filed: Apr. 30, 1976

[51] Int. Cl.² ............... A61H 19/00; A61F 7/00
[52] U.S. Cl. ............................. 128/24 A; 128/402
[58] Field of Search ............ 128/24 A, 24.1, 362, 128/399, 400, 402, 412

[56] References Cited

U.S. PATENT DOCUMENTS

| 2,970,073 | 1/1961 | Prange | 128/24 A |
| 3,499,437 | 3/1970 | Balamuth | 128/24 A |
| 3,867,929 | 2/1975 | Joyner et al. | 128/24 A |

FOREIGN PATENT DOCUMENTS

824,683  3/1951  Germany .................. 128/24 A

OTHER PUBLICATIONS

Fahim et al., "Heat in Male Contraception," Contraception, vol. 11, No. 5, May 1975, pp. 549-562.

*Primary Examiner*—Ronald L. Frinks
*Assistant Examiner*—Lee S. Cohen
*Attorney, Agent, or Firm*—Grace J. Fishel

[57] ABSTRACT

A method of suppressing spermatogenesis in domestic mammels having a scrotum by applying ultrasonic vibrations to the testes in said scrotum. More particularly, a method of suppressing spermatogenesis by sonicating the testes in said scrotum by immersing the scrotum in an ultrasonic coupling agent and applying ultrasonic vibrations thereto.

11 Claims, 4 Drawing Figures

METHOD OF MALE CONTRACEPTION FOR DOMESTIC MAMMALS HAVING A SCROTUM

This invention relates to the suppression of spermatogenesis in domestic mammals having a scrotum.

Recently, there has been growing concern about the plight of unwanted, stray pets. These homeless animals are sentenced to brutal deaths by the people who once owned them but, for one reason or another, no longer want them as pets. Condemned to the streets, sooner or later, many of these animals starve or freeze to death. Some are abused by unkind humans and some are hit by cars and left by the roadside to die.

Inflation has caused a few people to give up their pets, especially big dogs, but being unable to care for the animal is not the primary cause of strays. Primarily, the problem is caused by indiscriminate breeding.

Overpopulation of dogs and cats has been recognized by humane societies and shelters as a serious and growing problem. The Humane Society of the United States estimates that there are over 12,000,000 puppies and kittens born in the United States every year. It is no secret that the vast majority of those animals turned in at shelters are destroyed. This widespread extermination of unwanted animals is sickening, but the alternatives of street life are worse for the animal and pose a serious health problem to humans.

Animal waste is more than a joke on the bottom of the shoe. These deposits are not only bothersome, but they are also unhealthy. For example, according to a study in 1974 by U.S. News and World Report, dog feces can transmit over 40 human diseases, including mumps, measles, tuberculosis, diphtheria, scarlet fever, tape worm and ring worm.

The key to the problem is to prevent breeding, which up until now has been accomplished primarily by spaying the females. The seriousness of this operation with its attendant risks or the cost thereof, however, has deterred many owners from this method. Other methods, also cost prohibitive to some owners, have included castration of the males or, more recently, various birth control devices and pills. The latter methods, however, require more attention from the owner than most people are willing to give.

While castration of the male does prevent breeding and, once accomplished, requires no further attention, it has a number of undesirable side effects. It alters the level of male hormones in the blood which can affect the animal's sex characteristics and general health. Moreover, castration can change the nature of the animal and make it obese. It is also permanent, like spaying, and cannot be reversed.

Overpopulation of other domestic animals other than dogs and cats such as cattle, horses and the like is not a problem. However, in some cases, it is desirable to sterilize the male animal either to gentle it or to fatten it for butchering. In any case, clamping the testes with a pincer-like tool or cutting off the blood supply thereto with a constricting band have been the usual techniques. Clamping has the drawback that sometimes the urinary tract is cut with the result that the animal must be destroyed. This accidental cutting occurs even by skilled veterinarians and is a recognized risk in clamping. Clamping of the testes is also painful to the animal and because of this, unpleasant for the person doing the castrating.

In view of the above, there is need for a method of contraception which is painless to the animal and inexpensive to administer, and which causes temporary or permanent sterility as desired. For most purposes, particularly in the case of dogs and cats, there is need for such a method, which further has no effect on the animal's sex drive, sex characteristics or general health.

Therefore, among the several objects of the present invention may be noted the provision of a method for temporarily or permanently, as desired, sterilizing domestic mammals. This method is painless to the subject, inexpensive to apply and is, insofar as observed, totally without adverse effect on the animal's sex drive, sex characteristics or general health. Other objects and features will be in part apparent and in part pointed out hereinafter.

This invention accordingly comprises the methods hereinafter described, the scope of the invention being indicated in the subjoined claims. In the accompanying drawings, one example of the method as applied to dogs and the equipment useful therefor is illustrated. Corresponding reference characters indicate corresponding parts throughout the several views of the drawings, wherein, FIG. 1 is a perspective view of a dog being treated by the method of the present invention with his scrotum in a treatment device for sonicating the testes in said scrotum;

As before indicated, the present invention involves the application of ultrasonic vibrations to the testes of domestic mammals having an external pouch for the testes i.e., a scrotum. More particularly, the scrotum containing the testes is immersed in an ultrasonic coupling agent contained in a suitable vessel. The immersed scrotum is then sonicated with ultrasonic vibrations from an ultrasonic applicator which is constructed so that it can be placed in direct contact with the coupling agent in the vessel or so that its vibrations are passed thereto through the walls of the vessel.

Suitable subjects for said treatment include such domestic mammals as dogs, cats, cattle, sheep, horses, goats, hogs or the like, all of said subjects having an external pouch for the testes. When the subject animal is ready for treatment, it may be sedated. This is not necessary for the comfort of the subject since the treatment is not painful but is convenient for its administrator. This is particularly so in the case of animals other than dogs or the like which cannot be commanded to stand quietly.

If desired, the animal, preferably sedated, may be restrained on a holding device such as a table with an aperture through which its scrotum passes freely. In this position, the scrotum is easily accessible from beneath the table for treatment as above indicated and more particularly described hereinafter.

Figure 1:
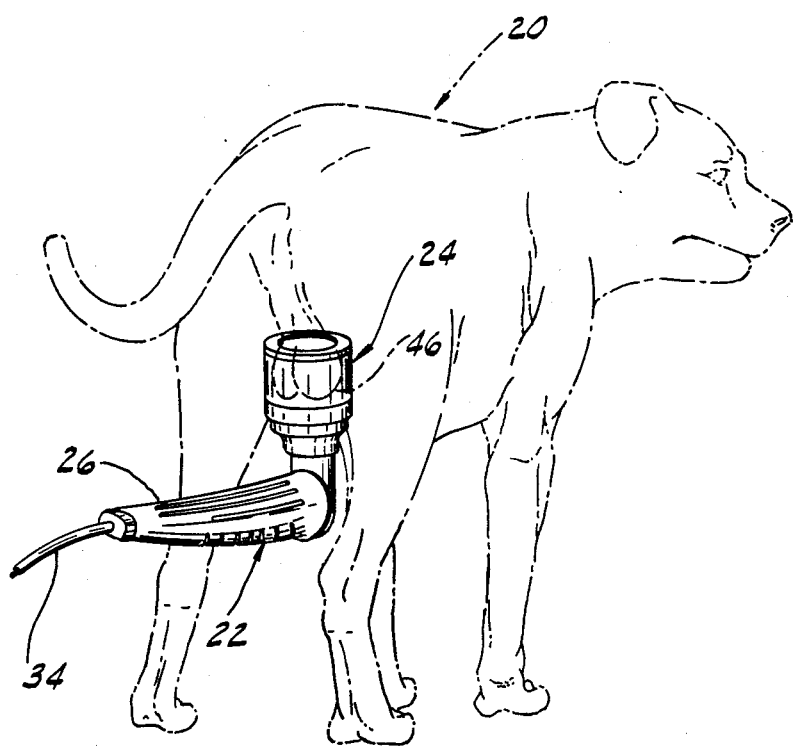

With a subject dog 20 standing as shown in FIG. 1, the invention will now be described with reference to the drawings. An ultrasonic applicator device such as applicator 22 is selected, said applicator having a cup 24 attached to a handle 26.

Applicator handle 26 consists of a casing 28 in which is mounted a transducer 30 at the end of a probe 32 for converting electrical energy from coaxial cable 34 into ultrasonic energy. Coaxial cable 34 is connected to an ultrasonic generator (not shown) but described below.

Figure 2:
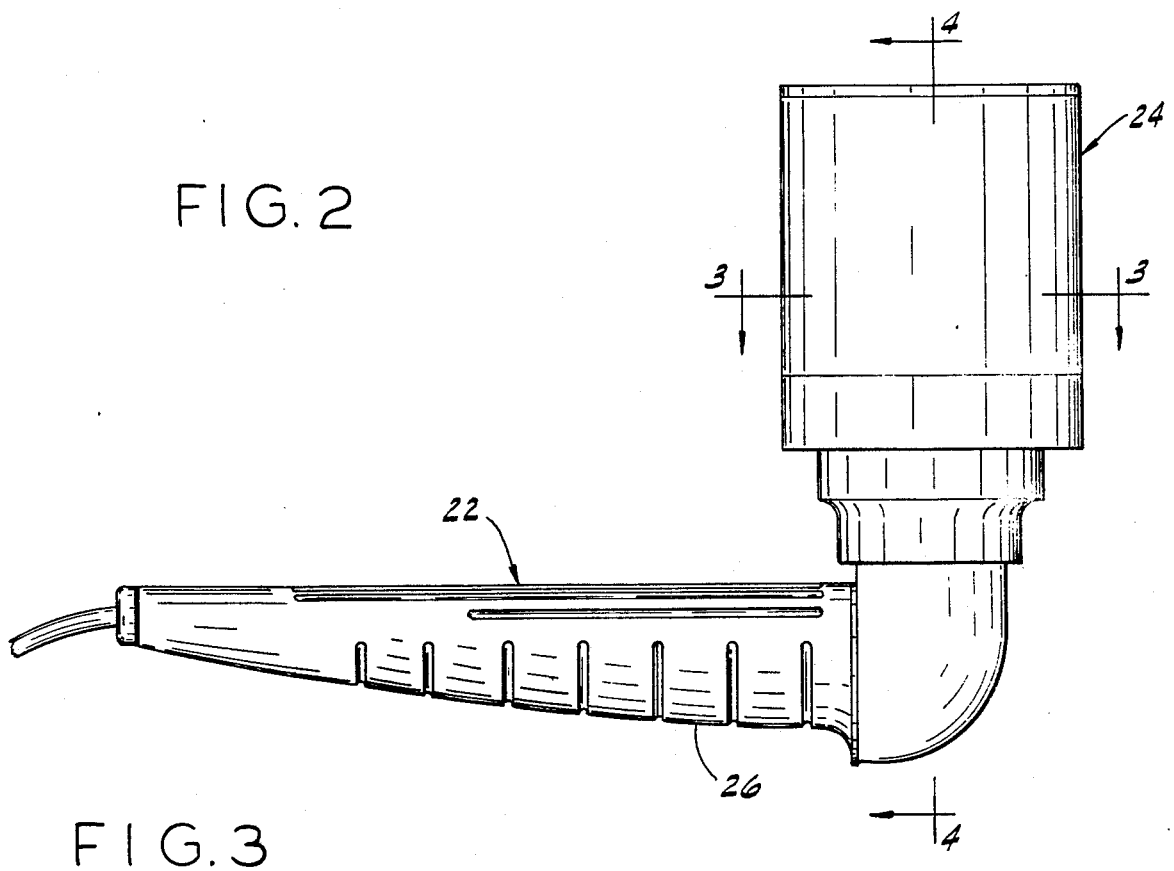
FIG. 2 is a side elevational view of the treatment device.
Figure 3:
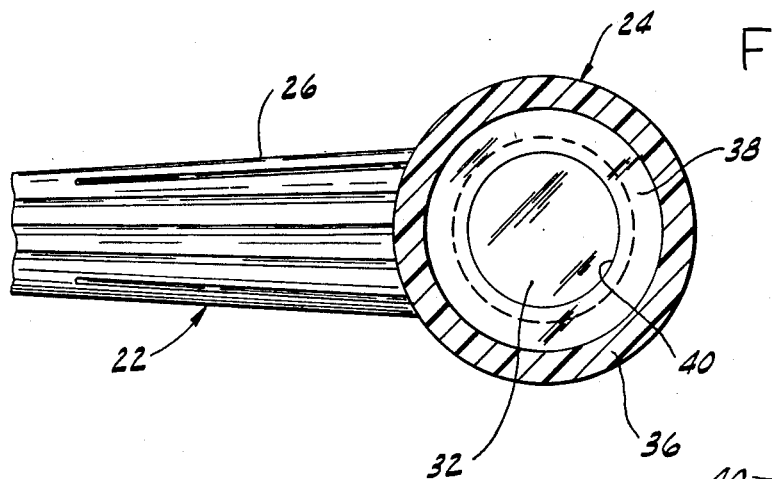
FIG. 3 is a horizontal cross-sectional view taken along line 3—3 in FIG. 2.
Figure 4:
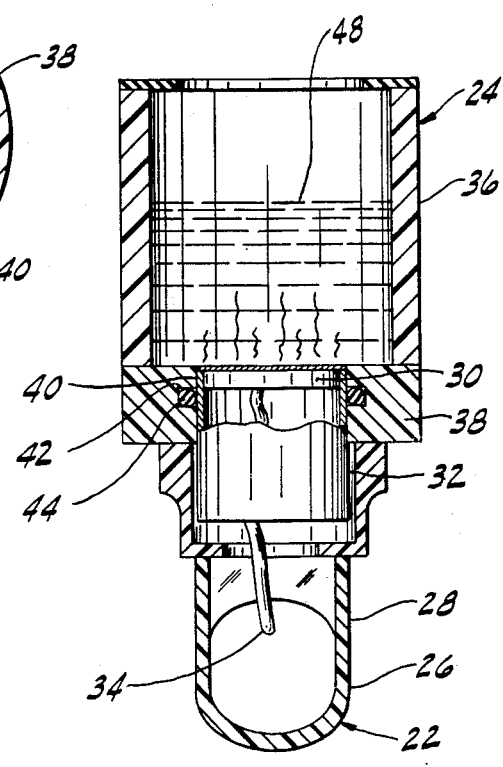
FIG. 4 is a vertical cross-sectional view taken along line 4—4 in FIG. 2.

As shown in FIGS. 2–4, cup 24 includes a cylindrical sidewall 36 which is sealed on one end to a bottom wall 38. Bottom wall 38 has an aperture 40 centrally located therein, said aperture having a recess 42 in the rim thereof. Probe 32 which provides a protective housing for transducer 30 is sealed in aperture 40 with an O-ring 44 which is fitted in recess 42 provided therefor. Probe 32 thus protects the transducer from the contents of cup 24. In other applicators (not shown), transducer 30 is cemented to bottom wall 38 which is constructed of material transparent to ultrasonic vibrations of the frequency herein employed. So constructed, of course, there is no aperture 40 in bottom wall 38.

Cup 24 should be selected of a size so that scrotum 46 of dog 20 may be contained therein. Preferably cup 24 is sized so that there is about one-fourth to about one-half inch clearance between said scrotum and sidewall 36 and bottom wall 38. Cups outside of this range may, however, be used under some circumstances. For this purpose, several different cups (not shown) should be provided in the treatment room so that one of the correct size may be selected. If cup 24 in applicator 22 is the wrong size, cup 24 is slipped from handle 26, O-ring 44 forming the frictional connection therebetween. Selected other cup 24 is then seated on handle 26 by its O-ring 44.

Since ultrasound does not transmit through air, a coupling agent must be provided in cup 24 to provide coupling between ultrasonic applicator 22 and scrotum 46. The particular coupling agent selected is preferably non-staining, non-irritating and slow evaporating. For this purpose, the agent is water or water mixed with other materials. Other coupling agents such as oils or the like are also contemplated.

After the subject has been prepared and cup 24 selected, it is filled with a coupling agent 48 and the animal's scrotum 46 immersed therein. The immersed scrotum is then treated with ultrasonic vibrations from applicator 22 transmitted through coupling agent 48 to the testes.

The length of the treatment, output frequency of the ultrasonic generator coupled to ultrasonic applicator 22 and power level at the applicator surface will vary in the individual case and is up to the treatment administrator. It has been found that generally the greater the energy applied to the testes in the scrotum, the more permanent is the suppression of spermatogenesis. It has also been found that the smaller the testes, the more permanent is the sterilization at a particular power level. Hence, the practical range of power depends upon the purpose of the treatment and the size of the testes. Very high power levels, however, should be avoided to prevent burning of the animal's skin. The most practical range is from about 0.25 to about 3 watt/cm$^2$ but the power level may go above or below that range. A preferred range is from about 0.5 to about 2 watt/cm$^2$ and a more preferred range is from about 0.5 to about 1 watt/cm$^2$.

Usually the frequency of the ultrasonic vibrations is within the range from about 500 to about 5000 KHZ. A preferred range is from about 500 to about 2500 KHZ and a particularly effective setting is 1100 KHZ $\pm$ 10 KHZ. Within the above-mentioned ranges, the suppression of spermatogenesis tends to be more permanent with increasing frequency, other treatment variables remaining constant.

The length and number of treatments also has an effect on the degree that spermatogenesis is suppressed. In general, it has been found that the longer the treatment, the more permanent is the suppression. Usually, the treatment is within the range from about 3 to about 15 min., but by varying the other treatment conditions, the duration can be increased or shortened as desired.

By selecting the treatment duration and the other treatment conditions, for example as described in the following examples, it is possible to completely and permanently sterilize the animal with only one treatment. On the other hand, if it is desired that multiple treatments be given periodically to induce temporary sterility or to induce permanent sterility gradually by sequential treatments, it has been found that treatment at 1100 KHZ $\pm$ 10 KHZ with 1 watt/cm$^2$ for 10 min. is effective. The degree of suppression can be determined by a sperm count. If the count is too high as to make impregnation of a female likely, treatment as described above is repeated, however, preferably but not necessarily after a wait of about 2 weeks. Again, a sperm count is taken and the treatent continued until the desired degree of suppression, either temporary or permanent, has been accomplished. The number of treatments to reduce the sperm count to zero or any other selected level depends on the animal's condition, including such factors as its age and general health.

The following examples illustrate the invention.

EXAMPLE 1

Fifteen male cats weighing 4.3 kg $\pm$ 0.5 were selected. These animals were sedated with 10 mg of ketamine/kg of body weight and divided into two groups, 5 in the control group and 10 in the treatment group. Plexiglass cups 24 having an inside diameter of about 4 cm and a depth of about 3 cm were selected, fitted on handle 26 of applicator 22 and filled with water as coupling agent 48.

Each animal's scrotum was immersed in the cup and the cup positioned by manipulation of handle 26 so that the animal's testicles approached within one-fourth to one-half inch of transducer 30.

Transducer 30 measured 11 cm$^2$ and was connected to an ultrasound generator manufactured by Whitewater Electronics, Inc. This generator had a frequency of 1100 KHZ and a continuous power output of 0 to 35 watts. With the power output of the ultrasound generator set so that the effective power level was 0 watt/cm$^2$ at transducer 30, the testes of the animals in the control group were treated for 10 min.

The treatment group was treated as described above except that the effective power level was 1 watt/cm$^2$. This group was then divided into two equal groups A and B, the cats in Group B were given a second treatment 48 hours after the first.

Testicular biopsies were taken from all the subject cats 60 days after treatment. Part of the testes were prepared for examination by light microscopy by immersing them in Bovin's solution for 48 hours. The testes were then transferred to 70% ethanol and embedded in paraplast. Four micron sections were cut, stained with hemotoxylin and eosin and examined under a light microscope.

Another part of the testes were prepared for examination by electron microscopy by cutting the seminiferous tubules into 3 mm lengths. The tubules were fixed first with 2% osmium tetroxide in 0.1 M phosphate buffer at pH 7.4 for 1 hour. This was followed by post-fixation in 3% glutaraldehyde in 0.1 M phosphate buffer at pH 7.4 for 1 hour.

The tubules were dehydrated with ethanol and embedded in Epon 812 according to standard procedure. When the blocks hardened thin sections were stained with uranyl acetate for 15 min. followed by lead citrate for 5 min. The sections were examined under an electron microscope.

For the control group, the results from light and electron microscopy showed normal numbers of sperm and normal spermatogenesis stages. For the cats in Group A of the treatment group, there were no sperm or spermatids in the tubules and a significant reduction in the number of secondary spermatocytes. The spermatogonia and sertoli cells, however, were intact indicating that the destruction of sperm and spermatid was temporary and that the tubules were capable of spermatogenesis and the animal, therefore, only temporarily sterilized.

The Lyding cell population and the blood testosterone level in group A, as in the control group, was found to be normal. This confirmed the observation that the animal's sex drive, sex characteristics and general health had not been affected by the treatment.

The results from light and electron microscopy for the cats in group B showed a complete lack of sperm, spermatid and secondary spermatocytes. There were no spermatogenesis stages noted indicating that sterilization was permanent because the tubules were no longer capable of spermatogenesis. The Lyding cell population and the blood testosterone level in group B, like the groups discussed above, was normal and the animals exhibited normal sex drive, sex characteristics and general health.

EXAMPLE 2

Twenty-four male dogs weighing 20 kg ± 2 were selected. These animals were prepared for treatment first by intromuscular injection of 1 cc atropine sulfate/15 pounds of body weight. After 10 min., the animals were sedated by intravenous injection of a 4% solution of thiamylal in an amount about 1 cc/5 pounds of body weight or until the animal went to sleep.

The animals were then divided into three equal treatment groups 1, 2 and 3. Plexiglass cups 24 having one of the following dimensions were selected depending upon the size of the testes: Cup A having an inside diameter of 4.9 cm and a depth of 4.5 cm., Cup B having an inside diameter of 6.9 mm and a depth of 5.5 cm and Cup C having an inside diameter of 8.2 cm and a depth of 5.8 cm. Selected cup 24 was fitted on handle 26 of applicator 22 and filled with water as coupling agent 48. A pre-treatment sperm count and blood testosterone level was taken and each animal's scrotum was immersed in the treatment cup, which was positioned so that the animal's testicles approached within one-fourth to one-half inch of transducer 30 in probe 32. Transducer 30 was identical to that described in Example 1 and was connected to a similar ultrasound generator which was set so that the effective power level was 1 watt/cm$^2$ at the transducer.

The animals in Groups 1, 2 and 3 were treated for 15 min. Those in Group 1 were treated once while those in Groups 2 and 3 were treated twice and three times, respectively. The interval between treatments was 48 hours. The blood testosterone level was determined periodically after treatment and was found to be the same as the pre-treatment level. The results of the sperm counts 1 week, 6 months and 1 year after treatment are reported in Table I on the following page.

TABLE I

| Group | Treatment | Presonification Sperm Count per 1ml | Sperm Count-1 week | Sperm Count-6 months | Sperm Count-1 year |
|---|---|---|---|---|---|
| 1 | 1 time | 233 × 10$^6$ | 40 × 10$^6$ | 210 × 10$^6$ | 280 × 10$^6$ |
| 2 | 2 times | 310 × 10$^6$ | 1 × 10$^6$ | 54 × 10$^6$ | 190 × 10$^6$ |
| 3 | 3 times | 270 × 10$^6$ | 0 × 10$^6$ | 0 × 10$^6$ | 2 × 10$^6$ |

EXAMPLE 3

Two male dogs were selected and treated like Group 1 of Example 2 except that the effective power level at transducer 30 was 2 watts/cm$^2$ and the treatment was continued for 20 min. No significant difference was noted in the blood testosterone level after treatment as compared to that before treatment. The sperm count, however, dropped from a normal level of 340 × 10$^6$ to 0 14 days after treatment.

In view of the above, it will be seen that the several objects of the invention are achieved and other advantageous results attained. For example, the administrator of the present method may temporarily or permanently sterilize the subject animal as he desires. The sterilized animal, however, experiences no pain during the treatment and has no change in libido thereafter.

As various changes could be made in the above methods without departing from the scope of the invention, it is intended that all matter contained in the above description or shown in the accompanying drawings shall be interpreted as illustrative and not in a limiting sense.

What is claimed is:

1. A method of suppressing spermatogenesis in domestic animals, excluding humans, having scrotal testes which comprises applying continuous ultrasonic vibrations selectively only to the testes of said animal at an effective power level and at a frequency sufficient to penetrate said scrotal testes and for a sufficient time to temporarily or permanently suppress spermatogenesis while causing the subject substantially no discomfort.

2. The method of suppressing spermatogenesis in domestic animals, excluding humans, having scrotal testes according to claim 1 wherein the continuous ultrasonic vibrations are transmitted by an ultrasound applicator connected to a continuous ultrasound generator, said continuous vibrations transmitted to said scrotal testes through a coupling agent in which said scrotal testes are immersed.

3. The method of suppressing spermatogenesis in domestic animals, excluding humans, having scrotal testes according to claim 2 wherein the coupling agent is contained in a vessel accommodating the scrotal testes to be sonicated.

4. The method of suppressing spermatogenesis in domestic animals, excluding humans, having scrotal testes according to claim 3 wherein the coupling agent is water.

5. The method of suppressing spermatogenesis in domestic animals, excluding humans, having scrotal testes according to claim 3 wherein the ultrasonic vibrations have a frequency between about 500 KHZ and about 5000 KHZ.

6. The method of suppressing spermatogenesis in domestic animals, excluding humans, having scrotal testes according to claim 5 wherein the effective power level of the ultrasound applicator is between about 0.25 watt/cm$^2$ and about 3 watt/cm$^2$.

7. The method of suppressing spermatogenesis in domestic animals, excluding humans, having scrotal testes according to claim 6 wherein the effective power level of the ultrasound applicator is between about 0.5 watt/cm$^2$ and about 2 watt/cm$^2$.

8. The method of suppressing spermatogenesis in domestic animals, excluding humans, having scrotal testes according to claim 7 wherein the effective power level of the ultrasound applicator is between about 0.5 watt/cm$^2$ and about 1 watt/cm$^2$.

9. The method of suppressing spermatogenesis in domestic animals, excluding humans, having scrotal testes according to claim 8 wherein the time is between about 3 min. and about 15 min.

10. The method of suppressing spermatogenesis in domestic animals, excluding humans, having scrotal testes according to claim 9 wherein the coupling agent is water and the ultrasonic vibrations have a frequency of 1100 KHZ ± 10 KHZ, the effective power level is 1 watt/cm$^2$ and the time is 10 min.

11. The method of suppressing spermatogenesis in domestic animals, excluding humans, having scrotal testes according to claim 10 wherein the effectiveness of the method is monitored by a sperm count, said method being repeated until the desired count is reached.

* * * * *

UNITED STATES PATENT AND TRADEMARK OFFICE
CERTIFICATE OF CORRECTION

PATENT NO. : 4,073,289
DATED : February 14, 1978
INVENTOR(S) : Mostafa S. Fahim

It is certified that error appears in the above-identified patent and that said Letters Patent are hereby corrected as shown below:

Abstract, line 2, "mammels" should read "mammals".

Column 4, line 48, after "1100 KHZ" insert "$\pm$ 10 KHZ".

Signed and Sealed this

Sixteenth Day of May 1978

[SEAL]

Attest:

RUTH C. MASON
Attesting Officer

LUTRELLE F. PARKER
Acting Commissioner of Patents and Trademarks